(12) United States Patent
Clements et al.

(10) Patent No.: US 10,028,531 B2
(45) Date of Patent: Jul. 24, 2018

(54) AEROSOL-GENERATING SYSTEM HAVING A PIERCING ELEMENT

(71) Applicant: PHILIP MORRIS PRODUCTS S.A., Neuchatel (CH)

(72) Inventors: Jeremy Peter Clements, Willingham (GB); Patrick-Charles Silvestrini, Neuchatel (CH); Alexandre Malgat, Les Tuileries de Grandson (CH)

(73) Assignee: Philip Morris Products S.A., Neuchatel (CH)

( * ) Notice: Subject to any disclaimer, the term of this patent is extended or adjusted under 35 U.S.C. 154(b) by 206 days.

(21) Appl. No.: 14/776,334

(22) PCT Filed: Mar. 12, 2014

(86) PCT No.: PCT/EP2014/054821
§ 371 (c)(1),
(2) Date: Sep. 14, 2015

(87) PCT Pub. No.: WO2014/140087
PCT Pub. Date: Sep. 18, 2014

(65) Prior Publication Data
US 2016/0029694 A1 Feb. 4, 2016

(30) Foreign Application Priority Data
Mar. 15, 2013 (EP) .................... 13159562

(51) Int. Cl.
*A24F 13/00* (2006.01)
*A24F 47/00* (2006.01)
(Continued)

(52) U.S. Cl.
CPC .......... *A24F 47/002* (2013.01); *A24F 47/004* (2013.01); *A61M 15/0028* (2013.01);
(Continued)

(58) Field of Classification Search
CPC .... A24F 47/002; A24F 47/004; A24F 47/006; A24F 47/008; A24B 15/16
(Continued)

(56) References Cited

U.S. PATENT DOCUMENTS 4,338,931 A 7/1982 Cavazza
4,793,365 A * 12/1988 Sensabaugh, Jr. ... A24B 15/165
128/202.21
(Continued)

FOREIGN PATENT DOCUMENTS

EP 1 867 357 A1 12/2007
EP 2 157 873 B1 7/2011
(Continued)

OTHER PUBLICATIONS

International Search Report dated Jul. 16, 2014 for PCT/EP2014/054821 filed on Mar. 12, 2014.
(Continued)

*Primary Examiner* — Hae Moon Hyeon
(74) *Attorney, Agent, or Firm* — Oblon, McClelland, Maier & Neustadt, L.L.P.

(57) ABSTRACT

An aerosol-generating system is provided, including an aerosol-generating device in cooperation with an aerosol-generating article. The article includes a first sealed compartment having a tubular porous element and a delivery enhancing compound sorbed thereon; and a second compartment having a volatile liquid. The device includes an outer housing adapted to receive the article; an elongate piercing member for piercing the first and second compartments. The elongate piercing member includes a piercing portion adjacent a distal end of the elongate piercing member; a shaft portion; and an obstructing portion adjacent a proximal end of the elongate piercing member. The piercing portion has a maximum diameter greater than the diameter
(Continued)

of the shaft portion, and the obstructing portion has an outer diameter such that it fits within the tubular porous element of the article when the article is received in the device. A corresponding aerosol-generating device and aerosol-generating article are also provided.

15 Claims, 5 Drawing Sheets

(51) Int. Cl.
*A61M 15/00* (2006.01)
*A61M 15/06* (2006.01)
*B05B 7/24* (2006.01)

(52) U.S. Cl.
CPC ........ *A61M 15/0035* (2014.02); *A61M 15/06* (2013.01); *B05B 7/2402* (2013.01); *A61M 15/004* (2014.02)

(58) Field of Classification Search
USPC ........................................................ 131/329
See application file for complete search history.

(56) References Cited

U.S. PATENT DOCUMENTS

| | | | | |
|---|---|---|---|---|
| 8,424,538 B2* | 4/2013 | Thomas | ............... | A24B 15/165 131/194 |
| 8,915,255 B2* | 12/2014 | Poget | ................... | A24B 15/165 131/360 |
| 2010/0186738 A1 | 7/2010 | Kobayashi et al. | | |
| 2012/0234821 A1 | 9/2012 | Shimizu | | |
| 2012/0255569 A1* | 10/2012 | Beard | ...................... | A24D 3/04 131/334 |

FOREIGN PATENT DOCUMENTS

| | | |
|---|---|---|
| EP | 2 520 186 A1 | 11/2012 |
| GB | 2 469 850 A | 11/2010 |
| GB | 2 473 264 A | 3/2011 |
| JP | 4-258281 A | 9/1992 |
| JP | 3074767 B2 | 8/2000 |
| JP | 2009-45441 A | 3/2009 |
| JP | 2010-506594 A | 3/2010 |
| RU | 103 281 U1 | 4/2011 |
| RU | 122 254 U1 | 11/2012 |
| WO | WO 2008/121161 A2 | 10/2008 |
| WO | WO 2008/121610 A1 | 10/2008 |
| WO | WO 2010/107613 A1 | 9/2010 |
| WO | WO 2011/034723 A1 | 3/2011 |
| WO | WO 2013/034458 A1 | 3/2013 |

OTHER PUBLICATIONS

Office Action dated Jan. 9, 2018 in Japanese Patent Application No. 2015-562118 (with English language translation).
Search Report dated Feb. 2, 2018 in Russian Patent Application No. 2015138114/12 (with English language translation).

* cited by examiner

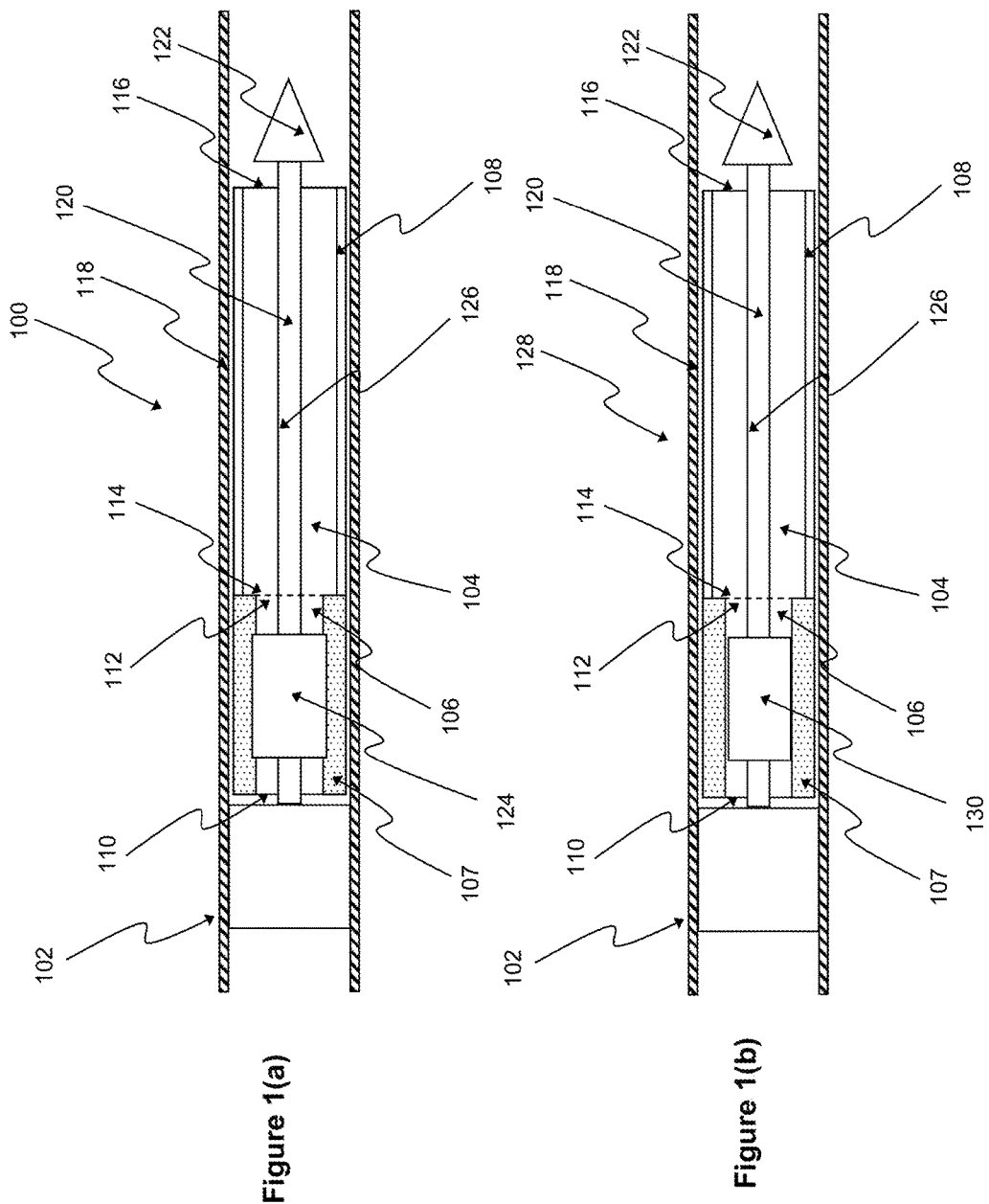

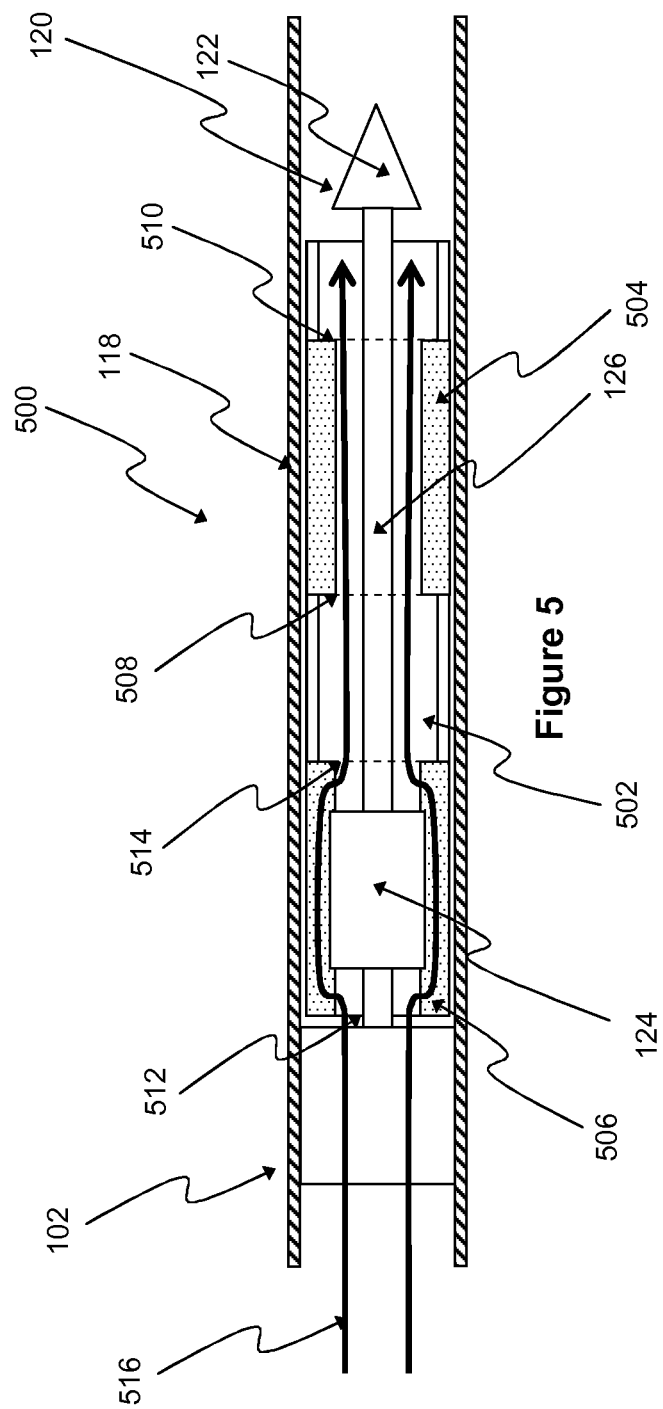

AEROSOL-GENERATING SYSTEM HAVING A PIERCING ELEMENT

CROSS REFERENCE TO RELATED APPLICATION

This application is a U.S. national phase application under 35 U.S.C. § 371 of PCT/EP2014/054821, filed on Mar. 12, 2014, and claims the benefit of priority under 35 U.S.C. § 119 from prior EP Application No. 13159562.1, filed on Mar. 15, 2013, the entire contents of each of which are incorporated herein by reference.

TECHNICAL FIELD

The present invention relates to an aerosol-generating system for delivering an aerosol to a user comprising an aerosol-generating device and an aerosol-generating article, and in particular to a smoking device for delivering aerosolised nicotine salt particles to a user. The invention further relates to an aerosol-generating device for receiving an aerosol-generating article.

DESCRIPTION OF THE RELATED ART

WO 2008/121610 A1 discloses devices and methods for delivering nicotine to a subject in which a delivery enhancing compound is reacted with nicotine in the gas phase to form an aerosol of nicotine salt particles. In order to retain the delivery enhancing compound, a sorption element on which the delivery enhancing compound is sorbed can be provided. The volatile delivery enhancing compound can be stored without degradation by oxidation, hydrolysis or other unwanted reactions by sealing the compartment in which the delivery enhancing compound is located.

However, to obtain a more complete reaction of the nicotine with the delivery enhancing compound aerosol, the mixing of the reactants in the gas phase needs to be addressed.

Thus, it would be desirable to provide such an aerosol-generating system which enables sufficient mixing of the volatile delivery enhancing compound and the nicotine or other medicament during use of the aerosol-generating system.

It would be also desirable to provide an aerosol-generating system for delivering nicotine or other medicament to a user of the type disclosed in WO 2008/121610 A1 in which the retention of one or both of the volatile delivery enhancing compound and the nicotine or other medicament during storage is improved. It would also be desirable to provide an aerosol-generating system for delivering nicotine or other medicament to a user of the type disclosed in WO 2008/121610 A1 in which the stability of one or both of the volatile delivery enhancing compound and the nicotine or other medicament during storage is maintained.

SUMMARY

According to a first aspect of the present invention, there is provided an aerosol-generating system comprising an aerosol-generating device in cooperation with an aerosol-generating article. The aerosol-generating article comprises a sealed first compartment comprising a tubular porous element and a delivery enhancing compound sorbed on the tubular porous element; and a second compartment comprising a volatile liquid. The aerosol-generating device comprises: an outer housing adapted to receive the aerosol-generating article; and an elongate piercing member for piercing the first compartment and the second compartment of the aerosol-generating article. The elongate piercing member comprises: a piercing portion adjacent a distal end of the elongate piercing member; a shaft portion; and an obstructing portion adjacent a proximal end of the elongate piercing member. The piercing portion has a maximum diameter greater than the diameter of the shaft portion, and the obstructing portion has an outer diameter such that it fits within the tubular porous element of the article when the aerosol-generating article is received in the device.

This may improve the mixing of the delivery enhancing compound and the volatile liquid by controlling the air flow through the aerosol-generating system.

BRIEF DESCRIPTION OF THE DRAWINGS

Embodiments will now be further described, by way of example only, with reference to the accompanying drawings in which:

FIGS. 1(a) and 1(b) show a schematic representation of aerosol-generating systems according to an embodiment of the present invention;

FIG. 5 shows an alternative embodiment of an aerosol-generating system.

DETAILED DESCRIPTION

Figure 2A:
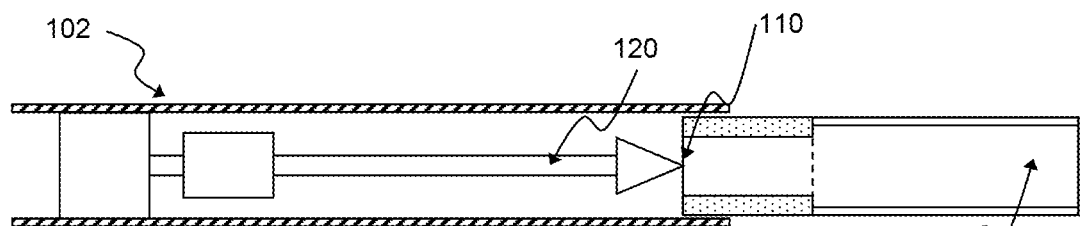
FIGS. 2(a) through 2(e) show an aerosol-generating article according to an embodiment of the present invention being inserted into an aerosol-generating device according to an embodiment of the present invention.

As used herein, the term "aerosol-generating device" refers to an aerosol-generating device that interacts with an aerosol-generating article to generate an aerosol that is directly inhalable into a user's lungs thorough the user's mouth.

As used herein, by "sorbed" it is meant that the delivery enhancing compound is adsorbed on the surface of the tubular porous element, or absorbed in the tubular porous element, or both adsorbed on and absorbed in the tubular porous element.

The aerosol-generating system may further comprise at least one air inlet upstream of the first compartment of the aerosol-generating article and at least one air outlet downstream of the second compartment of the aerosol-generating article, the at least one air inlet and the at least one air outlet being arranged when the aerosol-generating article is received in the aerosol-generating device to define an air flow pathway extending from the at least one air inlet to the at least one air outlet via the tubular porous element of the first compartment of the aerosol-generating article around the obstructing portion of the elongate piercing member of the aerosol-generating device, and via the second compartment of the aerosol-generating article around the shaft portion of the elongate piercing member of the aerosol-generating device. The second compartment may be downstream of the first compartment so that in use an air stream drawn through the aerosol-generating article passes through the first compartment and then passes through the second compartment.

In an alternative embodiment, the second compartment preferably comprises a tubular porous element, and the second compartment may be upstream of the first compartment so that in use an air stream drawn through the aerosol-generating article passes through the second compartment and then passes through the first compartment. In this alternative embodiment, the second compartment comprises a tubular porous element having the volatile liquid sorbed on the tubular porous element. The obstructing portion fits within the tubular porous element of the second compartment.

In this alternative embodiment, the aerosol-generating system may further comprise at least one air inlet upstream of the second compartment of the aerosol-generating article and at least one air outlet downstream of the first compartment of the aerosol-generating article, the at least one air inlet and the at least one air outlet being arranged when the aerosol-generating article is received in the aerosol-generating device to define an air flow pathway extending from the at least one air inlet to the at least one air outlet via the tubular porous element of the second compartment of the aerosol-generating article around the obstructing portion of the elongate piercing member of the aerosol-generating device, and via the first compartment of the aerosol-generating article around the shaft portion of the elongate piercing member of the aerosol-generating device.

As used herein, the terms 'upstream', 'downstream' and 'distal' and 'proximal' are used to describe the relative positions of components, or portions of components, of aerosol-generating articles, aerosol-generating devices and aerosol-generating systems according to the invention in relation to the direction of air drawn through the aerosol-generating articles, aerosol-generating devices and aerosol-generating systems during use thereof. It will be understood that the terms 'distal' and 'proximal', when used to describe the relative positions of components of the elongate piercing member, are used such that the piercing portion is at the distal, 'free', end and the obstructing portion is at the proximal, 'fixed', end which is connected to the device.

As used herein, the term "longitudinal" is used to describe the direction between the downstream or proximal end and the opposed upstream or distal end of the aerosol-generating article or aerosol-generating device and the term "transverse" is used to describe the direction perpendicular to the longitudinal direction.

The upstream and downstream ends of the aerosol-generating article are defined with respect to the airflow when a user draws on the proximal or mouth end of the aerosol-generating article. Air is drawn into the aerosol-generating article at the distal or upstream end, passes downstream through the aerosol-generating articles and exits the aerosol-generating article at the proximal or downstream end.

As used herein, the term "air inlet" is used to describe one or more apertures through which air may be drawn into the aerosol-generating system.

As used herein, the term "air outlet" is used to describe one or more aperture through which air may be drawn out of the aerosol-generating system.

In such embodiments, the first compartment and the second compartment are arranged in series from air inlet to air outlet within the aerosol-generating system. That is, the first compartment is downstream of the air inlet, the second compartment is downstream of the first compartment and the air outlet is downstream of the second compartment. In use, a stream of air is drawn into the aerosol-generating system through the air inlet, downstream through the first compartment and the second compartment and out of the aerosol-generating system through the air outlet.

In an alternative embodiment, the second compartment and the first compartment are arranged in series from air inlet to air outlet within the aerosol-generating system. That is, the second compartment is downstream of the air inlet, the first compartment is downstream of the second compartment and the air outlet is downstream of the first compartment. In use, a stream of air is drawn into the aerosol-generating system through the air inlet, downstream through the second compartment and the first compartment and out of the aerosol-generating system through the air outlet.

As used herein, by "series" it is meant that the first compartment and the second compartment are arranged within the aerosol-generating article so that in use an air stream drawn through the aerosol-generating article passes through one of the first compartment and the second compartment and then passes through the other of the first compartment and the second compartment. Delivery enhancing compound vapour is released from the delivery enhancing compound in the first compartment into the air stream drawn through the aerosol-generating article and volatile liquid vapour is released from the second compartment into the air stream drawn through the aerosol-generating article. The delivery enhancing compound vapour reacts with the volatile liquid vapour in the gas phase to form an aerosol, which is delivered to a user.

The piercing member is preferably positioned within the outer housing along the central longitudinal axis of the aerosol-generating device.

The obstructing portion preferably has a diameter relative to the internal diameter of the tubular porous element such that the bulk air flow through the aerosol-generating system flows through the tubular porous element. In this way, the delivery enhancing compound may be entrained in the air more effectively. To effect this air flow, where the obstructing portion has a diameter less than the internal diameter of the tubular porous element, the resistance to draw of the channel bounded by the obstructing portion and the inner surface of the tubular porous element is greater than the resistance to draw of the tubular porous element. The diameter of the obstructing portion may be between about 90% and about 100% of the internal diameter of the tubular porous element.

In a preferred embodiment, the obstructing portion has a diameter such that it forms an interference fit within the tubular porous element. As used herein, the term 'interference fit' is used to refer to a fit which substantially prevents air flow between the components having an 'interference fit'. The diameter of the obstructing portion may be between about 100% and about 150% of the internal diameter of the tubular porous element, preferably between about 110% and about 140%. In a preferred embodiment, the diameter of the obstructing portion is about 133% of the internal diameter of the tubular porous element.

The internal diameter of the tubular porous element is preferably between about 2 mm and about 5 mm, more preferably between about 2.5 mm and about 3.5 mm. In a preferred embodiment, the internal diameter of the tubular porous element is about 3 mm.

The diameter of the obstructing portion is preferably between about 1.5 mm and about 7.5 mm, more preferably between about 3 mm and about 5 mm. In a preferred embodiment, the diameter of the obstructing portion is about 4 mm.

The maximum diameter of the piercing portion is preferably equal to or less than the diameter of the obstructing portion. More preferably, the maximum diameter of the piercing portion is between about 75% and about 100% of the diameter of the obstructing portion, and yet more preferably is between about 90% and about 100% of the obstructing portion.

The maximum diameter of the piercing portion is preferably between about 105% and about 125% of the diameter of the shaft portion. More preferably, the maximum diameter of the piercing portion is between about 110% and about 120% of the diameter of the shaft portion. In a preferred embodiment, the maximum diameter of the piercing portion is about 120% of the diameter of the shaft portion.

The obstructing portion preferably has a longitudinal length of between about 25% and about 75% of the longitudinal length of the tubular porous element. More preferably the obstructing portion has a longitudinal length of between about 40% and about 60% of the longitudinal length of the tubular porous element, and in one embodiment the obstructing portion has a longitudinal length of about 50% of the longitudinal length of the tubular porous element.

The obstructing portion is preferably arranged to be positioned centrally, along the longitudinal axis of the device, within the tubular porous element when the aerosol-generating article is received inserted in the device.

The tubular porous element preferably has a longitudinal length of between about 7.5 mm and about 15 mm, more preferably of between about 9 mm and about 11 mm, and in the preferred embodiment the tubular porous element has a longitudinal length of about 10 mm.

The obstructing portion preferably has a longitudinal length of between about 1.5 mm and about 9.5 mm, more preferably between about 3 mm and about 7 mm, and in the preferred embodiment the obstructing portion has a longitudinal length of about 5 mm.

In a preferred embodiment the tubular porous element is a hollow cylinder. The hollow cylinder is preferably a right circular hollow cylinder.

The piercing portion preferably has a maximum diameter of between about 75% and about 100% of the internal diameter of the hollow cylinder.

In a preferred embodiment the piercing portion is conical. However, it should be understood that the piercing portion may be of any shape suitable for piercing the compartments of the aerosol-generating article. Where the piercing portion is conical, the maximum diameter of the piercing portion corresponds to the diameter of the base circle of the cone.

The maximum diameter of the piercing portion is preferably between about 1.5 mm and about 5 mm, more preferably between about 1.75 mm and about 3.5 mm. In a preferred embodiment, the piercing portion has a maximum diameter of about 3 mm.

The second compartment is preferably a hollow cylinder, and the piercing portion preferably has a maximum diameter of between about 50% and about 75% of the internal diameter of the second compartment.

The second compartment preferably has an internal diameter of between about 4 mm and about 8 mm, more preferably between about 5 mm and about 7 mm. In a preferred embodiment the second compartment has an internal diameter of about 6.5 mm.

The second compartment preferably has a longitudinal length of between about 20 mm and about 50 mm, more preferably between about 30 mm and about 40 mm. In a preferred embodiment the second compartment has a longitudinal length of about 35 mm.

The longitudinal length of the elongate piercing member is preferably greater than the total longitudinal length of the first compartment and the second compartment. Providing a piercing member having such a length enables the first compartment and the second compartment of the aerosol-generating article to be pierced using only the elongate piercing member.

The shaft of the piercing member preferably has a diameter of between about 1 mm and about 3 mm, more preferably between about 1.5 mm and about 2.5 mm. In a preferred embodiment the shaft has a diameter of about 2 mm. The shaft of the piercing member is provided with a smaller diameter than the maximum diameter of the piercing portion so that, in use, air can flow around the shaft and through the holes formed in the first and second compartments by the piercing portion.

The second compartment is preferably sealed.

Preferably a first end of the first compartment is sealed by a frangible barrier, an interface between a second end of the first compartment and a first end of the second compartment is sealed by at least one frangible barrier, and a second end of the second compartment is sealed by a frangible barrier. In a preferred embodiment, each end of the first compartment and each end of the second compartment is sealed by a frangible barrier.

Preferably, each of the first compartment and the second compartment comprises a frangible barrier at each end. The frangible barrier is configured such that the barrier can be pierced by the piercing member when the aerosol-generating article is inserted into the aerosol-generating device by the user.

Preferably, each frangible barrier is made from metal film, and more preferably from aluminium film.

Preferably, the first compartment and the second compartment of the aerosol-generating article abut one another. Alternatively, the first compartment and the second compartment may be spaced apart.

The volume of the first compartment and the second compartment may be the same or different. In a preferred embodiment, the volume of the second compartment is greater than the volume of the first compartment.

The aerosol-generating article preferably further comprises at least one further element. The aerosol-generating article may further comprise one, two, three, four, five or more further elements. The further element may be any of: a filter element; a third compartment; an aerosol forming chamber; and a hollow tube. In a preferred embodiment the further element comprises a mouthpiece. The mouthpiece may be sealed at the proximal end of the aerosol-generating article.

The mouthpiece may comprise any suitable material or combination of materials. Examples of suitable materials include thermoplastics that are suitable for food or pharmaceutical applications, for example polypropylene, polyetheretherketone (PEEK) and polyethylene.

In a preferred embodiment the outer housing of the aerosol-generating device comprises a cavity configured to receive the aerosol-generating article. Preferably, the cavity has a longitudinal length greater than the longitudinal length of the elongate piercing member. In this way, the piercing portion of the piercing member is not exposed, or accessible by the user.

Preferably, the cavity of the aerosol-generating device is substantially cylindrical. The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the aerosol-generating article to be received in the cavity.

The aerosol-generating system may further comprise a power supply, at least one heater, and control circuitry. The control circuitry is preferably configured to control the supply of power to the at least one heater such that the delivery enhancing compound and the volatile liquid are sufficiently volatilised to enable the generation of an aerosol.

The overall dimensions of the aerosol-generating system may be similar to a conventional smoking article such as a cigarette, a cigar a cigarillo or any other such smoking article.

In use, the user inserts the aerosol-generating article into the outer housing of the aerosol-generating device. As the user inserts the aerosol-generating article, the piercing member pierces a first end of the first compartment, passes through the hollow central portion of the tubular porous element, and then pierces a second end of the first compartment. The piercing member then pierces a first end of the second compartment (where included), passes through the second compartment and then pierces a second end of the second compartment (where included), and the obstructing portion fits within the tubular porous element so as to define the air flow pathway described herein. The user then draws on the proximal end of the aerosol-generating article causing air to flow along the air flow pathway, entraining delivery enhancing compound vapour from the delivery enhancing compound sorbed on the porous tubular element of the first compartment and volatile liquid vapour from the volatile liquid in the second compartment. An aerosol is generated by the delivery enhancing compound vapour reacting with the volatile liquid vapour in the gas phase. The generation of the aerosol is described in further detail below.

In the alternative embodiment, where the second compartment comprises a tubular porous element, and the second compartment is upstream of the first compartment, the aerosol-generating system functions as follows. In use, the user inserts the aerosol-generating article into the outer housing of the aerosol-generating device. As the user inserts the aerosol-generating article, the piercing member pierces a first end of the second compartment, passes through the tubular porous element, and then pierces a second end of the second compartment. The piercing member then pierces a first end of the first compartment, passes through the first compartment and then pierces a second end of the first compartment. The obstructing portion fits within the tubular porous element of the second compartment so as to define the air flow pathway described herein with reference to the alternative embodiment. The user then draws on the proximal end of the aerosol-generating article causing air to flow along the air flow pathway, entraining volatile liquid vapour from the volatile liquid on the tubular porous element in the second compartment, and entraining delivery enhancing compound vapour from the delivery enhancing compound sorbed on the porous tubular element of the first compartment. An aerosol is generated by the delivery enhancing compound vapour reacting with the volatile liquid vapour in the gas phase.

According to a further aspect of the present invention, there is provided an aerosol-generating device for an aerosol-generating system as described herein. The aerosol-generating device comprises: an outer housing adapted to receive an aerosol-generating article, the aerosol-generating article having a first compartment having a tubular porous element and a second compartment; and an elongate piercing member configured to pierce the first compartment and the second compartment of the aerosol-generating article when an aerosol-generating article is received in the outer housing. The elongate piercing member comprises: a piercing portion adjacent a distal end of the elongate piercing member; a shaft portion; and an obstructing portion adjacent a proximal end of the elongate piercing member. The piercing portion has a maximum diameter greater than the diameter of the shaft portion, and the obstructing portion has an outer diameter such that it fits within the tubular porous element of the first compartment of the aerosol-generating article when an aerosol-generating article is received in the device.

As used herein, the term "aerosol-generating device" refers to an aerosol-generating device that interacts with an aerosol-generating article to generate an aerosol that is directly inhalable into a user's lungs thorough the user's mouth.

According to a yet further aspect of the present invention, there is provided an aerosol-generating article for an aerosol-generating system. The aerosol-generating article comprises: a first compartment having a first end and a second end, comprising a tubular porous element and a delivery enhancing compound including an acid sorbed on the porous tubular element; and a second compartment comprising a volatile liquid including a nicotine formulation having a first end, adjacent the second end of the first compartment, and a second end. The first end of first compartment is sealed by a frangible barrier, the interface between the second end of the first compartment and the first end of the second compartment is sealed by at least one frangible barrier, and the second end of the second compartment is sealed by a frangible barrier.

Preferably each end of each of the first compartment and second compartment is sealed by a frangible barrier. Preferably, the first compartment and the second compartment are formed separately and combined together by abutting the second end of the first compartment with the first end of the second compartment and wrapping both compartments in a wrapper material. The wrapper material may be card or any other suitable material. The wrapper material may extend past the second end of the second compartment to form a mouthpiece or aerosol forming chamber.

The first compartment of the aerosol-generating article preferably comprises a volatile delivery enhancing compound. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid or ammonium chloride. Preferably, the delivery enhancing compound comprises an acid. More preferably, the delivery enhancing compound comprises an acid having a vapour pressure of at least about 5 Pa at 20° C. Preferably, the acid has a greater vapour pressure than nicotine at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the delivery enhancing compound comprises an alpha-hydroxy, an alpha-keto or 2-oxo acid.

In a preferred embodiment, the delivery enhancing compound comprises an acid selected from the group consisting of lactic acid, 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the delivery enhancing compound comprises pyruvic acid.

The tubular porous element is preferably a sorption element with an acid or ammonium chloride sorbed thereon.

The tubular porous element may be formed from any suitable material or combination of materials for sorbing a liquid. The tubular porous element may comprise one or more porous materials selected from the group consisting of porous plastic materials, porous polymer fibres and porous glass fibres. The one or more porous materials may or may not be capillary materials and are preferably inert with respect to the acid or ammonium chloride. The particular preferred porous material or materials will depend on the physical properties of the acid or ammonium chloride. The one or more porous materials may have any suitable porosity so as to be used with different acids having different physical properties. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Suitable porous fibrous materials include, but are not limited to: cellulose cotton fibres, cellulose acetate fibres and bonded polyolefin fibres, such as a mixture of polypropylene and polyethylene fibres.

The size, shape and composition of the tubular porous element may be chosen to allow a desired amount of volatile delivery enhancing compound to be sorbed on the tubular porous element.

In a preferred embodiment, between about 15 μl and about 200 μl, more preferably between about 40 μl and about 150 μl, most preferably between about 50 μl and about 100 μl of the volatile delivery enhancing compound is sorbed on the tubular porous element.

The tubular porous element advantageously acts as a reservoir for the delivery enhancing compound.

Preferably, the second compartment comprises a source of nicotine. As such, the volatile liquid within the second compartment preferably comprises one or more of nicotine, nicotine base, a nicotine salt, or a nicotine derivative.

The source of nicotine may comprise natural nicotine or synthetic nicotine. The source of nicotine may comprise nicotine base, a nicotine salt, such as nicotine-HCl, nicotine-bitartrate, or nicotine-ditartrate, or a combination thereof.

The source of nicotine may further comprise an electrolyte forming compound. The electrolyte forming compound may be selected from the group consisting of alkali metal hydroxides, alkali metal oxides, alkaline earth metal oxides, sodium hydroxide (NaOH), calcium hydroxide ($Ca(OH)_2$), potassium hydroxide (KOH) and combinations thereof.

Alternatively or in addition, the source of nicotine may further comprise other components including, but not limited to, natural flavours, artificial flavours and antioxidants.

Preferably, the second compartment comprises a liquid nicotine formulation. Preferably, the second compartment is configured to hold between about 5 microliters and about 50 microliters of the liquid nicotine formulation, more preferably about 10 microliters of the liquid nicotine formulation.

The liquid nicotine formulation may comprise pure nicotine, a solution of nicotine in an aqueous or non-aqueous solvent or a liquid tobacco extract.

The liquid nicotine solution may comprise an aqueous solution of nicotine base, a nicotine salt, such as nicotine-HCl, nicotine-bitartrate, or nicotine-ditartrate and an electrolyte forming compound.

The second compartment may comprise a sorption element and nicotine sorbed on the sorption element. In a preferred embodiment, the second compartment comprises a volatile liquid nicotine source.

In a preferred embodiment, the aerosol-generating article further comprises an aerosol forming chamber in fluid communication with the first compartment and the second compartment. In use, in a preferred embodiment the nicotine reacts with the acid or ammonium chloride in the gas phase in the aerosol forming chamber to form aerosolised nicotine salt particles.

Alternatively, the delivery enhancing compound vapour may react with the nicotine vapour in the second compartment. In such embodiments the aerosol-generating article may further comprise a third compartment downstream of the second compartment and the delivery enhancing compound vapour may alternatively or in addition react with the nicotine vapour in the third compartment to form an aerosol.

The invention allows a cost effective, compact and easy to use aerosol-generating system to be provided. Furthermore, by using an acid or ammonium chloride as a delivery enhancing agent in aerosol-generating articles according to the invention, the pharmacokinetic rate of the nicotine may be advantageously increased.

It will be understood that the aerosol-generating system may also be regarded as an aerosol delivery system. That is to say, the aerosol-generating system provides means for the volatile liquid, such as a nicotine formulation, and the delivery enhancing compound, such as a pyruvic acid, to mix and generate an aerosol but does not actively generate the aerosol. In the embodiment where the aerosol-generating article comprises a third compartment, the third compartment is preferably downstream of the second compartment. Where the article comprises an aerosol forming chamber, the third compartment is preferably downstream of the aerosol forming chamber. The third compartment may comprise a flavour source. Alternatively or in addition, the third component may comprise a filtration material capable of removing at least a portion of any unreacted acid or ammonium chloride mixed with aerosolised nicotine salt particles drawn through the third compartment. The filtration material may comprise a sorbent, such as activated carbon. As will be appreciated, any number of additional compartments may be provided as desired. For example, the article may comprise a third compartment comprising a filter material and a fourth compartment downstream of the third compartment comprising a flavour source.

As will be appreciated, a number of factors influence the formation of the nicotine salt particles. In general, in order to control the nicotine delivery it is important to control the vaporisation of the nicotine formulation and the acid or ammonium chloride. It is also important to control the relative quantities of the nicotine and the acid or ammonium chloride. In the preferred embodiment, the molar ratio of acid to nicotine in the aerosol forming chamber is about 1:1. The use of acid or ammonium chloride as a delivery enhancing compound has been found to approximately double the delivery rate of nicotine to a user for equivalent power supplied to the vaporiser.

The vaporisation of the acid or ammonium chloride is controlled by the concentration of the acid or ammonium chloride in the first compartment, and by the exchange surface area of acid or ammonium chloride in the first compartment. The vaporisation of the acid or ammonium chloride may be controlled by heating the first compartment of the aerosol-generating article or by heating ambient air drawn through the device before it passes through the first compartment of the aerosol-generating article. In preferred embodiments where the first compartment comprises pyruvic acid, preferably about 60 micrograms of pyruvic acid is vaporised per puff.

Providing an obstructing portion enables the quantity of delivery enhancing compound vaporised per puff to be increased as compared to an aerosol-generating system without such an obstructing portion.

Preferably, the article comprises an opaque outer housing. This advantageously reduces the risk of degradation of the acid or ammonium chloride and nicotine formulation due to exposure to light.

Preferably, the cartridge is not refillable. Thus, when the nicotine formulation in the second compartment of the aerosol-generating article has been used up, the aerosol-generating article is replaced.

In certain embodiments, the device as well as the aerosol-generating article may be disposable.

Advantageously, all elements of the device which are potentially in contact with the acid or ammonium chloride or the source of nicotine are changed when the aerosol-generating article is replaced. This avoids any cross-contamination in the device between different mouthpieces and different aerosol-generating articles, for example aerosol-generating articles comprising different acids or sources of nicotine.

The nicotine formulation in the second compartment may be advantageously protected from exposure to oxygen (because oxygen cannot generally pass through the barrier of the second compartment until it is pierced by the piercing member) and in some embodiments light, so that the risk of degradation of the nicotine formulation is significantly reduced. Therefore, a high level of hygiene can be maintained.

The aerosol-generating article is preferably substantially cylindrical in shape. The aerosol-generating article may have a transverse cross-section of any suitable shape. Preferably, the aerosol-generating article is of substantially circular transverse cross-section or of substantially elliptical transverse cross-section. More preferably, the aerosol-generating article is of substantially circular transverse cross-section.

Preferably, the aerosol-generating article has a transverse cross-section substantially the same shape as the cavity of the aerosol-generating device.

A housing of the aerosol-generating article may simulate the shape and dimensions of a tobacco smoking article, such as a cigarette, a cigar, a cigarillo or a pipe, or a cigarette pack. In a preferred embodiment, the housing simulates the shape and dimensions of a cigarette.

The aerosol-generating device and aerosol-generating article may be arranged to releasably lock together when engaged.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol-generating system and device are preferably portable. The aerosol-generating system may have a size and shape comparable to a conventional smoking article, such as a cigar or cigarette.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

FIG. 1(a) shows a schematic representation of an aerosol-generating system 100. The system 100 comprises an aerosol-generating device 102 and an aerosol-generating article 104. The aerosol-generating article 104 has an elongate cylindrical shape and comprises a first compartment 106 comprising a volatile delivery enhancing compound source, and a second compartment 108 comprising a volatile liquid nicotine source. The first compartment 106 and the second compartment 108 are arranged in series and abut each other in axial alignment. The first compartment 106 is positioned at the distal, or upstream, end of the aerosol-generating article 104. The second compartment 108 is positioned downstream of the first compartment. A further element (not shown) in the form of a mouthpiece or the like may be provided at the downstream end of the second compartment.

The upstream and downstream ends of the first compartment 106 and the second compartment 108 of the aerosol-generating article 104 are sealed by frangible barriers 110, 112 and 114, 116 respectively. The frangible barriers are made from metal film, such as aluminium.

The aerosol-generating device 102 comprises an outer housing 118 having an elongate cylindrical cavity configured to receive the aerosol-generating article 104. The longitudinal length of the cavity is less than the length of the article 104 such that the proximal, or downstream, end of the article 104 protrudes from the cavity.

The device 102 further comprises an elongate piercing member 120. The piercing member is positioned centrally within the cavity of the aerosol-generating device and extends along the longitudinal axis of the cavity. At the proximal end the piercing member 120 comprises a piercing portion 122 in the form of a cone having a circular base. At the distal end the piercing member further comprises an obstructing portion 124 which, in use, acts as a flow restrictor and forms a desired air flow pathway. The piercing portion 122 and the obstructing portion 124 are mounted on a shaft 126.

Air inlets (not shown) are provided at the distal, upstream, end of the aerosol-generating device 102. Air outlets (not shown) are provided at the proximal, downstream, end of the aerosol-generating article 104.

FIG. 1(b) shows a similar aerosol-generating system 128 as that shown in FIG. 1(a), and like numerals have been used to reference similar components. As can be seen, the diameter of the obstructing portion 130 is such that it fits within the tubular porous element 107 to act as a flow restrictor to form a desired air flow pathway as described herein.

FIGS. 2(a) to 2(e) show the article 104 being inserted into the device 102. FIG. 2(a) shows the piercing member 120 engaging with the article 104. The piercing portion 122 breaks the frangible barrier 110 and creates a hole in the barrier having a diameter approximately equal to the maximum diameter of the piercing portion. The maximum diameter of the piercing portion is the diameter of the base circle of the cone which forms the piercing portion. As can be seen the internal diameter of the device cavity relative to the external diameter of the article 104 is such that the article is located centrally within the cavity.

Figure 2B:
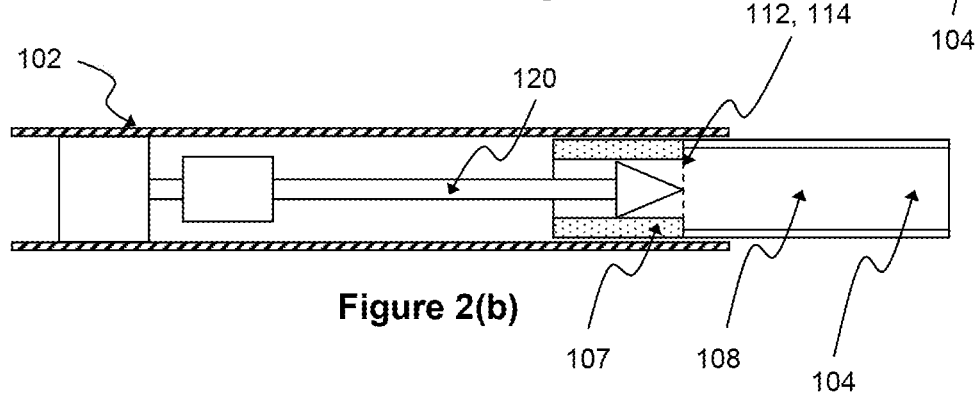

FIG. 2(b) shows the piercing portion engaging with the second frangible barrier of the first compartment 106. Again, the piercing portion breaks the frangible barrier 112 and creates a hole in the barrier having a diameter approximately equal to the maximum diameter of the piercing portion. As can be seen, the maximum diameter of the piercing portion is approximately equal to the internal diameter of the tubular porous element 107. At this stage, the piercing portion also breaks through the first frangible barrier 114 of the second compartment 108, and creates a hole in the barrier having a diameter approximately equal to the maximum diameter of the piercing portion.

Figure 2C:
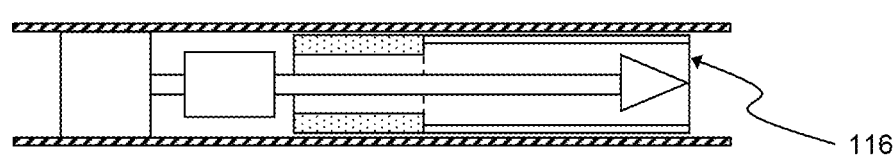

FIG. 2(c) shows the piercing engaging with the second frangible barrier of the second compartment. Again, the piercing portion breaks the frangible barrier 116 and creates a hole in the barrier having a diameter approximately equal to the maximum diameter of the piercing portion.

Figure 2D:
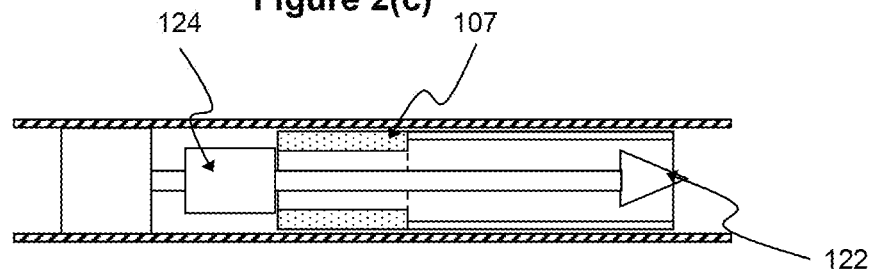

FIG. 2(d) shows the obstructing, flow restrictor, portion 124 engaging with the tubular porous element 107. As can be seen, the external diameter of the obstructing, flow restrictor, portion is larger than the internal diameter of the tubular porous element such that it forms an interference fit in the tubular porous element. The main function of the interference fit is to define the air flow pathway, as described in further detail below, but the interference fit may also aid in the retention of the article within the device during use.

Figure 2E:
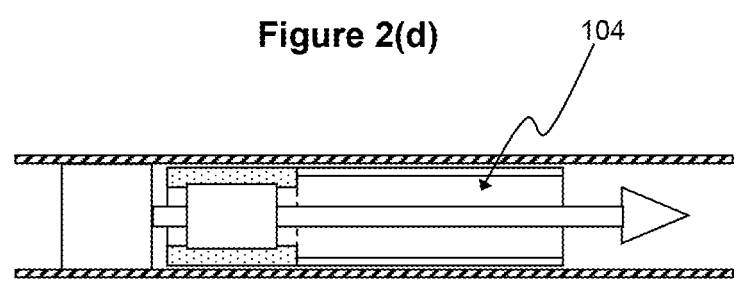

FIG. 2(e) shows the article 104 fully inserted into the device, ready for use. As can be seen, the obstructing, flow restrictor, portion is positioned centrally within the tubular porous element 107, and the piercing portion 122 extends past the proximal, downstream, end of the second compartment.

Figure 3:
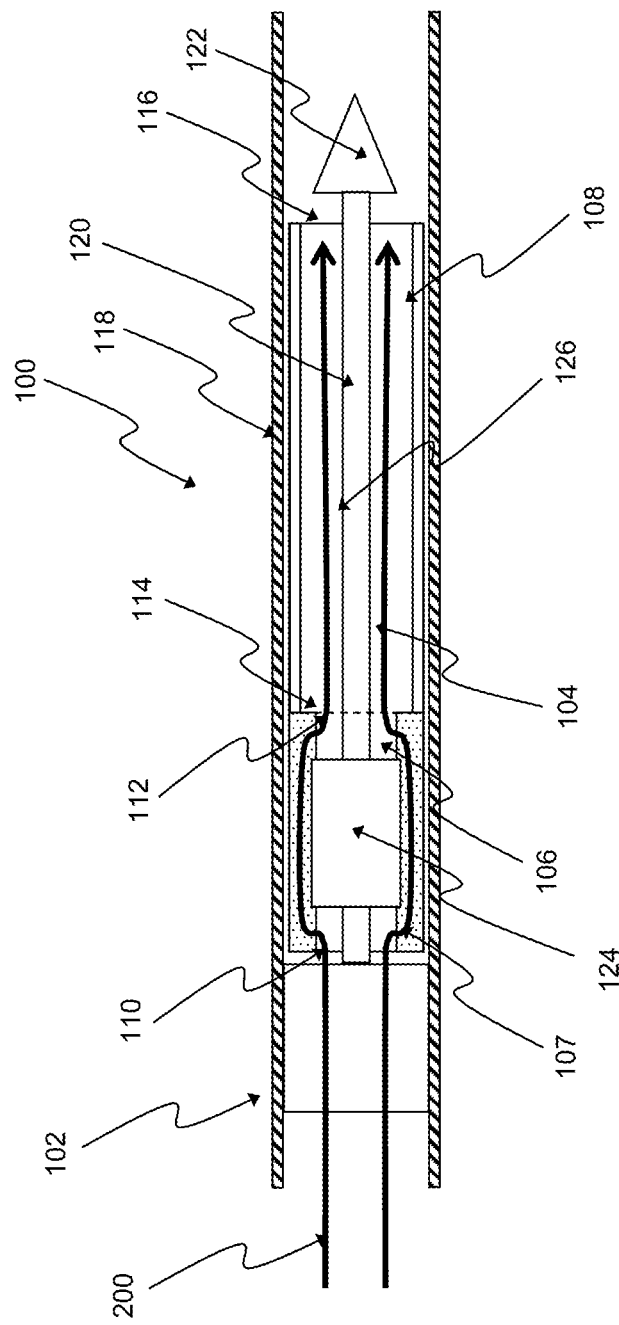
FIG. 3 shows the air flow pathway through the aerosol-generating system of FIG. 1.

As shown in FIG. 3, in use, when the aerosol-generating article 104 is fully inserted into the aerosol-generating device 102, an air flow pathway, shown by the arrows 200, is formed through the aerosol-generating system. The air flow pathway extends from the distal, upstream end of the aerosol-generating article 104 through the air inlets to the proximal, downstream, end of the article 104. The obstructing, flow restrictor, portion 124 ensures that the air flow pathway extends through the tubular porous element 107.

In use, and as described above, as the aerosol-generating article 104 is inserted into the cavity of the aerosol-generating device 102 the piercing member 120 is inserted into the aerosol-generating article 104 and pierces the frangible barriers 110, 112, 114 and 116 at the upstream and downstream ends of the first compartment 107 and second compartment 108 of the aerosol-generating article 104. This allows a user to draw air into the aerosol-generating article through the air inlets at the distal, upstream, end thereof, downstream through the tubular porous element 106, and the second compartment 108 and out of the article through the air outlets at the proximal, downstream, end thereof. The obstructing, flow restrictor, portion 124 ensures that the air flow pathway extends through the porous material of the tubular porous element 107. The air flow pathway extends about the shaft of the piercing member via the hole made in the frangible barriers 112, and 114 by the piercing portion 122. The air flow pathway further extends about the shaft of the piercing member via the hole made in the frangible barrier 116 at the proximal, downstream end of the second compartment, and then about the piercing portion 122. By providing a shaft having a smaller diameter than the maximum diameter of the piercing portion, the air flow pathway is enabled to extend around the shaft in the region of the frangible barrier.

Delivery enhancing compound vapour, which in the preferred embodiment contains pyruvic acid, is released from the delivery enhancing compound sorbed on the tubular porous element 107 into the air stream drawn through the aerosol-generating article 104 and nicotine vapour is released from the volatile liquid nicotine source in the second compartment 108 into the air stream drawn through the aerosol-generating article 104. The delivery enhancing compound vapour reacts with the nicotine vapour in the gas phase in the second compartment 108 to form an aerosol, which is delivered to the user through the proximal, downstream, end of the aerosol-generating article 104.

Figure 4:
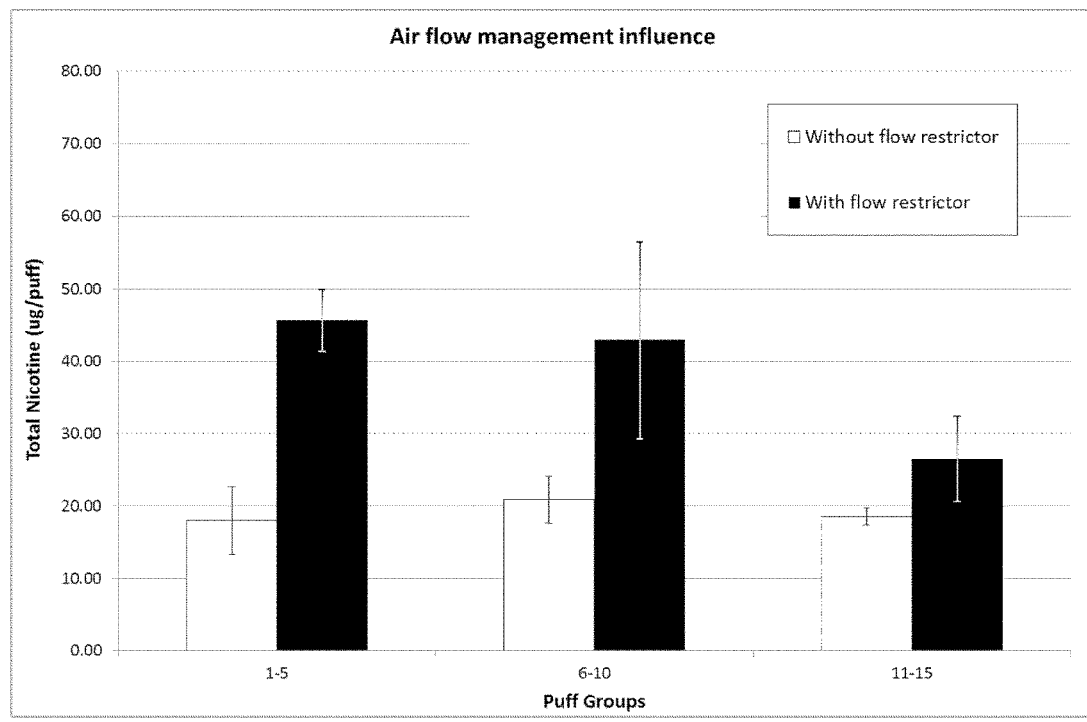
FIG. 4 shows a graph of test data showing the improved nicotine delivery for an aerosol-generating system having an obstructing portion which acts as a flow restrictor.

FIG. 4 shows experimental data which compares the nicotine delivery per five puffs of the aerosol-generating system with and without the obstructing, flow restrictor, portion on the piercing member. As can be seen, inclusion of the obstructing, flow restrictor, portion increases the overall mass of nicotine delivered over the total of 15 puffs by over 100%.

FIG. 5 shows a schematic representation of an aerosol-generating system 500. The system 500 comprises an aerosol-generating device 102, which is the same as that described above in relation to FIGS. 1(a) to 3, and an aerosol-generating article 502. The aerosol-generating article 502 has an elongate cylindrical shape and comprises a first compartment 504 comprising a delivery enhancing compound source, and a second compartment 506 comprising a volatile liquid nicotine source. The first compartment 504 and the second compartment 506 are arranged in series and are in axial alignment. The first compartment 504 and the second compartment 506 each comprise a tubular porous element for sorbing the respective liquids stored therein.

The first compartment 504 is positioned at the proximal, or downstream, end of the aerosol-generating article 502. The second compartment 506 is positioned upstream of the first compartment. As will be appreciated, the order of the compartments in this embodiment is opposite to the order of the compartments in the embodiment described in relation to FIGS. 1(a) to 3. Again, a further element (not shown) in the form of a mouthpiece or the like may be provided at the downstream end of the second compartment.

The upstream and downstream ends of the first compartment 504 and the second compartment 506 of the aerosol-generating article 502 are sealed by frangible barriers 508, 510 and 512, 514 respectively. The frangible barriers are made from metal film, such as aluminium.

Air outlets (not shown) are provided at the proximal, downstream, end of the aerosol-generating article 502.

In this embodiment, the obstructing portion 124, fits in the tubular porous portion of the second compartment 506, and ensures that the airflow pathway 516 extends through the tubular porous element of the second compartment 506. The airflow entrains nicotine, which in turn passes through the first compartment 504 comprising the delivery enhancing compound. The delivery enhancing compound reacts with the nicotine vapour in the gas phase in the first compartment 504 to form an aerosol, which is delivered to the user through the proximal, downstream, end of the aerosol-generating article 502.

The invention has been exemplified above by reference to aerosol-generating systems comprising aerosol-generating devices comprising a piercing member having a conical piercing portion. However, it will be appreciated that aerosol-generating systems and aerosol-generating devices according to the invention may comprise other forms of piercing portion.

The invention claimed is:

1. An aerosol-generating system, comprising:
an aerosol-generating device in cooperation with an aerosol-generating article;
the aerosol-generating article comprising:
a first sealed compartment comprising a tubular porous element and a delivery enhancing compound sorbed on the tubular porous element, and
a second compartment comprising a volatile liquid;
the aerosol-generating device comprising:
an outer housing configured to receive the aerosol-generating article, and
an elongate piercing member for piercing the first compartment and the second compartment of the aerosol-generating article,
wherein the elongate piercing member comprises:
a piercing portion adjacent a distal end of the elongate piercing member,
a shaft portion, and
an obstructing portion adjacent a proximal end of the elongate piercing member, and
wherein the piercing portion has a maximum diameter greater than the diameter of the shaft portion, and the obstructing portion has an outer diameter such that the obstructing portion fits within the tubular porous element of the aerosol-generating article when the aerosol-generating article is received in the aerosol-generating device.

2. The aerosol-generating system according to claim 1, further comprising at least one air inlet upstream of the first compartment and at least one air outlet downstream of the second compartment, the at least one air inlet and the at least one air outlet being arranged to define an air flow pathway extending from the at least one air inlet to the at least one air outlet via the tubular porous element of the first compartment around the obstructing portion, and via the second compartment around the shaft portion.

3. The aerosol-generating system according to claim 1, wherein the second compartment comprises a tubular porous element, the system further comprising at least one air inlet upstream of the second compartment and at least one air outlet downstream of the first compartment, the at least one air inlet and the at least one air outlet being arranged to define an air flow pathway extending from the at least one air inlet to the at least one air outlet via the tubular porous element of the second compartment around the obstructing portion, and via the first compartment around the shaft portion.

4. The aerosol-generating system according to claim 1, wherein the obstructing portion has a diameter such that it forms an interference fit within the tubular porous element.

5. The aerosol-generating system according to claim wherein the obstructing portion has a longitudinal length of between about 25% and about 75% of the longitudinal length of the tubular porous element.

6. The aerosol-generating system according to claim 5, wherein the maximum diameter of the piercing portion has a maximum diameter of between about 75% and about 100% of the internal diameter of the hollow cylinder.

7. The aerosol-generating system according to claim 1, wherein the tubular porous element is a hollow cylinder.

8. The aerosol-generating system according to claim 1, wherein the second compartment is a hollow cylinder, and the piercing portion has a maximum diameter of between about 50% and about 75% of the internal diameter of the second compartment.

9. The aerosol-generating system according to claim 1, wherein the longitudinal length of the elongate piercing member is greater than the total longitudinal length of the first compartment and the second compartment.

10. The aerosol-generating system according to claim 1, wherein the piercing portion is conical.

11. The aerosol-generating system according to claim 1, wherein the article further comprises a mouthpiece.

12. The aerosol-generating system according to claim 1, wherein a first end of the first compartment is sealed by a frangible barrier, an interface between a second end of the first compartment and a first end of the second compartment is sealed by at least one frangible barrier, and a second end of the second compartment is sealed by a frangible barrier.

13. The aerosol-generating system according to claim 12, wherein each frangible barrier is made from metal film.

14. An aerosol-generating device for an aerosol-generating system, comprising:
- an outer housing configured to receive an aerosol-generating article, the aerosol-generating article having a first sealed compartment having a tubular porous element and a second compartment; and
- an elongate piercing member configured to pierce the first compartment and the second compartment of the aerosol-generating article when the aerosol-generating article is received in the outer housing,
- wherein the elongate piercing member comprises:
  - a piercing portion adjacent a distal end of the elongate piercing member,
  - a shaft portion, and
  - an obstructing portion adjacent a proximal end of the elongate piercing member, and wherein the piercing portion has a maximum diameter greater than the diameter of the shaft portion, and the obstructing portion has an outer diameter such that the obstructing portion fits within the tubular porous element of the aerosol-generating article when the aerosol-generating article is received in the aerosol-generating device.

15. An aerosol-generating article for an aerosol-generating system, comprising:
- a first sealed compartment having a first end and a second end, comprising a tubular porous element and a delivery enhancing compound including an acid sorbed on the tubular porous element; and
- a second sealed compartment having a first end, adjacent the second end of the first compartment, and a second end, comprising a volatile liquid including a nicotine formulation,
- wherein the first end of first compartment is sealed by a frangible barrier, an interface between the second end of the first compartment and the first end of the second compartment is sealed by at least one frangible barrier, and the second end of the second compartment is sealed by a frangible barrier.

* * * * *